US006458760B1

(12) United States Patent
Seyfried et al.

(10) Patent No.: US 6,458,760 B1
(45) Date of Patent: Oct. 1, 2002

(54) METHOD FOR TREATING TISSUE DAMAGED FROM ISCHEMIA

(75) Inventors: Donald M. Seyfried, Plymouth; John Anagli, Walled Lake, both of MI (US)

(73) Assignee: Henry Ford Health System, Detroit, MI (US)

( * ) Notice: Subject to any disclaimer, the term of this patent is extended or adjusted under 35 U.S.C. 154(b) by 0 days.

(21) Appl. No.: 09/439,705

(22) Filed: Nov. 12, 1999

Related U.S. Application Data

(60) Provisional application No. 60/108,049, filed on Nov. 12, 1998.

(51) Int. Cl.$^7$ .......................... A61K 37/18; A61K 38/06
(52) U.S. Cl. ............................... 514/2; 514/17; 514/19; 530/331; 530/332
(58) Field of Search .............................. 514/2, 17, 19; 530/331, 332

(56) References Cited

U.S. PATENT DOCUMENTS

| 5,055,451 A | * | 10/1991 | Krantz et al. .................. 514/19 |
| 5,223,486 A | * | 6/1993 | Gordon et al. ................. 514/18 |
| 5,486,623 A | * | 1/1996 | Zimmerman et al. ........ 519/417 |
| 5,610,297 A | * | 3/1997 | Powers ........................ 544/168 |
| 5,691,368 A | * | 11/1997 | Peet et al. .................... 514/376 |

OTHER PUBLICATIONS

Seyfried et al., *J. Neurosurg.*, vol. 87, pp. 716–723, 1997.*
Seyfried et al., *Neurosurg.*, vol. 88, p. 203A, poster #44, Jan. 1998.*
Anagli, John, et al., "Investigation of the role of calpain as a stimulus–response mediator in human platelets using new synthetic inhibitors", *Biochem. j.*, (1991), 274, 497–502.
Anagli, John, et al., "Affinity labelling of the Ca$^{2+}$–activated neutral proteinase (calpain) in intact human platelets", *Biochem. j.*, (1993), 289, 93–99.
Angliker, Herbert, et al., "Inactivation of calpain by Peptidyl Fluoromethyl Ketones", *Journal of Med. Chemistry*, (1992), 35(2), 216–220.
Bederson, Joshua, et al., "Rat Middle Cerebral Artery Occlusion: Evaluation of the Model and Development of a Neurologic Examination", *Stroke*, (1986), 17(3), 472–476.

Crawford, Catherine, et al. "The design of peptidyldiazomethane inhibitors to distinguish between the cystein proteinases calpain II, cathepsin L and cathepsin B", *Biochem.*, (1988) 253, 751–758.
George, Green, et al., "Peptidy Diazomethyl Ketones are Specific Inactivators of Thiol Proteinases", *The Journal of Bio. Chem.*, (1981), 256, 1923–1928.
Kitz, R., et al., "Esters of Methanesulfonic Acid as Irreversible Inhibitors of Acetylcholinesterase", *The Journal of Bio. Chem.*, (1962), 237(10), 3245–3249.
Mellgren, Ronald, et al. "Inhibition of Growth of Human TE2 andC–33A Cells by the Cell–Permeant calpain Inhibitor Benzyloxycarbonyl–Leu–Leu–Tyr Diazomethyl ketone", *Experimental Cell Res.*, (1994), 215, 164–171.
Seyfried, Donald M., "Cathepsin B Activity and Expression Following Focal Cerebral Ischemia in the Rat", *Stroke*, (1996), 27(1):191.
Seyfried, Donald M., "A Novel Treatment Reduces Cerebral Infarction in a Preclinical Study of Middle Cerebral Artery Occlusion and Reperfusion", *Stroke*, (1997), 28(1) :254.
Seyfried, Donald M., "Cathepsin B and L Selective Cysteine Protease Inhibitors Reduce Cerebral Infarction After Transient Middle Cerebral Artery Ischemica", *J. Neurosurg.*, (1998), 88: 203A.
Seyfried, Donald M., "Cathepsin B and middle cerebral artery occlusion in the rat", *J. Neurosurg.*, (1997), 87:716–723.
Tian, Wei–Xi, et al., "Determination of the Rate Constance of Enzyme Modification by Measuring the Substrate Reaction in the Presence of the Modifier", *Biochemistry*, (1982), 21, 1028–1032.

\* cited by examiner

*Primary Examiner*—Christopher S. F. Low
*Assistant Examiner*—Abdel A. Mohamed
(74) *Attorney, Agent, or Firm*—Scully, Scott, Murphy & Presser

(57) ABSTRACT

The present invention relates to a method for treating tissue damage caused by ischemia in a patient which comprises administering to said patient a therapeutically effective amount of a compound which is an inhibitor of cathepsin B or cathepsin L, but which is not as an effective inhibitor of calpain relative to cathepsin B or cathepsin L or both and which compound is a peptidyl diazomethyl ketone.

41 Claims, No Drawings

METHOD FOR TREATING TISSUE DAMAGED FROM ISCHEMIA

RELATED APPLICATIONS

This application is claiming benefit of U.S. Ser. No. 60/108,049, filed on Nov. 12, 1998.

FIELD OF THE INVENTION

The present invention is directed to a method for treating tissue damage in a mammal caused by ischemia, such as from a stroke or from myocardial ischemia, utilizing a peptidyl diazomethyl ketone.

BACKGROUND OF THE INVENTION

An ischemia is a deficiency of blood flow to a body part, due to functional constriction or actual obstruction of a blood vessel. Ischemia may occur in various parts of the body of an animal, but it has the most dire consequences when it occurs in the brain, in the heart or in the bowels.

For example, a stroke occurs when there is an interruption of blood flow to an area of the brain. It is usually caused by an embolism or clot that blocks a significant artery in the brain. Blood flow to this area is blocked, causing the affected tissue to become hypoxic. Upon resolution of the cause of the stroke, at least partial blood flow is restored to the affected tissue of the animal. These two processes, lack of blood flow and then restoration of blood flow both produce effects that damage the affected brain tissue.

Among the mechanism of damage initiated by stroke is the activation of calcium sensitive proteases due to the influx of calcium ions into the hypoxic tissue.

At least two classes of proteases, the calpains and the cathepsins, are believed to be activated during cerebral ischemia. Both enzymes are cysteine proteases, the former being located in the cytoplasm, while the latter is located in the lysosome of the cells. Brain tissue contains the cathepsins B, L, S, and H, of which the first two predominate. Moreover, at physiological pH, cathepsin L is less stable than cathepsin B.

Both the calpains and cathepsins play a role in the basal recycling of neural cytoskeletal components. These enzymes are part of a series of enzymes which includes phospholipases, phosphatases, certain kinases and proteases, and which participate in this recycling process.

Cathepsins have been studied under conditions of cardiac ischemia and are believed to play a role in tissue damage by their release from the lysosome into the cytoplasm, where they are able to contribute to cellular injury by the breakdown of cellular structural components. Increased intracellular calcium and acidic pH are believed to be factors leading to lysosomal membrane instability and the activation of these proteases during cardiac ischemia. The same phenomena of calcium influx and acidosis occurs following brain ischemia, and these are believed to cause further cellular damage.

Because tissue perfusion is required for the distribution of pharmaceuticals to target tissues, it is difficult to intervene pharmacologically in the stroke process to prevent the damage caused by hypoxia that occurs during stroke. Thus, the objective of medical research in this area is to reduce the amount of time that the tissue is hypoxic and simultaneously therewith to develop therapies to prevent the activation of the destructive processes that ensues upon restoration of blood flow. In this regard, attention has been focused on the calpains and cathepsins and inhibitors of these two protease classes have been proposed for treating patients afflicted with brain ischemia, myocardial ischemia, and other diseases.

A number of investigators have indeed suggested that calpain inhibition could reduce stroke damage. These cytosolic neutral cysteine proteases are thought to trigger release of the lysosomal proteases. Reduction in tissue damage resulting therefrom has been observed in some experimental systems. However, these results are often complicated by the use of calpain inhibitors that also inhibit a number of other proteases.

Recently, U.S. Pat. No. 4,518,825 to Rasnik, discloses that α-amino fluoroketone peptide derivatives inhibit various proteases, including serine and cysteine proteases, including, but not limited to cathepsins B, H, C, G, R; elastase; trypsin; plasma kallikrein; glandular kallikrein; plasmin; plasminogen activator; and the like. These compounds, however, exhibit non-specific binding to serine proteases, as well as other non-cathepsin cysteine proteases.

Krantz, et al. in U.S. Pat. No. 5,055,451 disclose aryloxy and arylacyloxy methylketones as thiol protease inhibitors, including inhibitors of Cathepsin B. Krantz, et al. recognized that there is a need for potent and specific thiol protease inhibitors and in particular a need for chemically stable inhibitors that minimize the likelihood of non-specific reactions with plasma or cellular constituents. Unfortunately, the aryloxy and arylacyloxy compounds displayed unacceptable toxicity in large animals.

PCT Application WO 96/21655 and U.S. Pat. No. 5,691,368 to Peet disclose oxazolidine inhibitors of calpain and/or cathepsin B; it is alleged that the compounds are useful in the treatment of patients afflicted with acute or chronic neurodegenerative disorders.

EPO Application 525,420 to Ando, et al. disclose peptidyl aminomethylketones that exhibit reversible inhibition of calpains and cathepsins. They allege that these compounds are clinically useful in the treatment of various diseases, including stroke.

It is to be noted that in each of these references, the compounds disclosed therein inhibit a number of enzymes, including but not limited to both cathepsins and calpains. None of the references disclose inhibitors that are specific for only one type of cysteine protease. However, as recognized by both Rasnik and Krantz, et al. described hereinabove, for a drug in this field to be effective, it must not only interact with one type of cysteine protease, but, in addition, there must also be a lack of interaction with other cysteine proteases to prevent unwanted side effects.

The present, inventors, however have found such a system. In particular, they have found that peptidyl diazomethyl ketones, and in particular, N-terminus amino protected diazomethyl ketones such as benzyloxy-carbonyl peptidyl diazomethyl ketones, are capable of specifically inhibiting cathepsins significantly better than calpains.

Benzyloxycarbonyl peptidyl diazomethyl ketones, however, are not new compounds, but have been described in earlier publications by Shaw, et al. For example, Shaw, et al. in *Arch. Biochem. Biophys*, 1983, 222, 424–429 reveal a number of benzyloxycarbonyl-Phe-X-$CHN_2$ derivatives, wherein X is one of several amino acids or derivatized amino acids and their effect on the in vitro activity of bovine spleen cathepsins. However, these compounds were not considered viable clinical candidates for treating damaged tissues because, as indicated by Powers in U.S. Pat. No. 5,610,297, these compounds are thought, inter alia, to be poorly membrane permeant and to have low specificity.

But, the present inventors have surprisingly found that these compounds are not poorly membrane permeants and do not have low specificity.

SUMMARY OF THE PRESENT INVENTION

Accordingly, the present invention is directed to treating tissue damage in a patient caused by ischemia comprising administering to said patient a therapeutically effective amount of a compound which is an inhibitor of at least one of cathepsin B or cathepsin L, wherein the inhibition of cathepsin B or L is significantly greater than that of calpain, said compound being a peptidyl diazomethyl ketone and more preferably a N-terminus amino protected peptidyl diazomethyl ketone.

DETAILED DESCRIPTION OF THE INVENTION

The present invention is directed to a method for treating tissue damage in a mammal resulting from ischemia. The compounds useful for this purpose are small lipophilic molecules which are specific inhibitors of cathepsin B or cathepsin L or both. They may inhibit cathepsin B, but not cathepsin L or vice versa or they may inhibit both enzymes. However, it is a significantly poorer inhibitor of calpain relative to either cathepsin B or cathepsin L.

Another characteristic of the present invention is that the compounds utilized are peptidyl diazomethyl ketones. These compounds are preferably di or tri-peptides. In addition, they have a molecular weight ranging from about 450 to about 1000 daltons.

A preferred embodiment of the present invention has the formula:

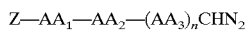
$$Z-AA_1-AA_2-(AA_3)_n CHN_2 \qquad I$$

wherein
- Z is H or an amino protecting group at the N-terminus;
- n is 0 or 1;
- $AA_1$ is a hydrophobic amino acid residue;
- $AA_3$ is a hydrophobic amino acid residue, a hydroxy or thiol containing amino acid or a ether or thioether containing amino acid; and
- $AA_2$ is α-amino isobutyric acid or a hydrophobic amino acid residue when n is 1 but when n is 0, $AA_2$ is a hydrophobic amino acid residue, a hydroxy or thiol containing amino acid or an ether or thioether containing amino acid.

A more preferred embodiment of the present invention has Formula I, wherein
- Z, n and $AA_1$ are as defined hereinabove;
- $AA_3$ is a hydrophobic amino acid residue, $AA_5 (OR_{12})$ or $AA_5 (SR_{12})$; and
- $AA_2$ is α-amino butyric acid or a hydrophobic amino acid residue when n is 1; but when n is 0, $AA_2$ is a hydrophobic amino acid residue or $AA_4(OR_{11})$ or $AA_4 (SR_{11})$ or Met, wherein
  - $AA_5$ and $AA_4$ are the same or different amino acids which have the OH group or thiol group or thiomethyl group on the side chain is removed;
  - $R_{11}$ and $R_{12}$ are independently hydrogen, lower alkyl, aryl, aryl lower alkyl, heterocyclic or heterocyclic lower alkyl.

An even more preferred embodiment has Formula I

$$Z-AA_1-AA_2-(AA_3)_n CHN_2 \qquad I$$

wherein
- Z is H or an amino protecting group at the N-terminus;
- n is 0 or 1;
- $AA_1$, $AA_2$ and $AA_3$ are amino acid residues;
- $AA_1$ is a hydrophobic amino acid residue;
- $AA_3$ is a naturally occurring hydroxy or thiol containing amino acid residue or hydrophobic acid;
- $AA_2$ is α-amino isobutyric acid (Aib) or a hydrophobic amino acid residue when n is 1; but when n is 0, $AA_2$ is Met, Cit, Aib, Ala, Trp, Ser($OR_4$), Thr($OR_5$), Tyr, hTry, Tyr($R_9$) ($OR_6$), hTyr($R_9$) ($OR_6$), Cys($SR_7$), hCys ($SR_7$), hPhe($R_8$), hSer($OR_4$) or Phe($R_8$);
- hCys is homocysteine;
- hPhe is homophenylalanine;
- hSer is homoserine;
- hTyr is homotyrosine;
- $R_4$, $R_5$, $R_6$ and $R_7$ are independently hydrogen, aryl, aryl lower alkyl, bulky alkyl group or lower alkyl,
- $R_8$ is hydrogen or an electron withdrawing group; and
- $R_9$ is a substituent on the phenyl ring of the tyrosine and is hydrogen or an electron withdrawing group.

As used herein, the term "amino acid residue" refers to an amino acid less the hydrogen atom on the N-terminus and less the hydroxy group on the C-terminus end thereof. Various designations, such as the 3 letter or 1 letter abbreviations, have been utilized to represent the amino acids. When these abbreviations are used, it is to be understood that these are abbreviations of amino acid residues, as defined herein. Thus, for example, Ala is

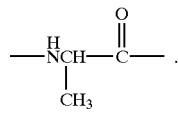

It is preferred that the amino acid is a natural amino acid. It is also preferred that the amino acids are α-amino acids.

The amino acids contemplated to be used therein include the natural amino acids and derivatives thereof. More specifically, the amino acids utilized herein may be analogs or homologs of the natural amino acids. For example, the side chain may contain alkylene groups bridging the alpha carbon atom on the amino acid and the side chain. The bridging alkylene groups may be lower alkylene containing 1–6 carbon atoms. Preferably, these bridging alkylene groups contain 1–3 carbon atoms and most preferably contain 1 carbon atom. For example, the naturally occurring side chain of phenylalanine is benzyl. A homolog contemplated and to be within the scope of the amino acid utilized in the present invention is a bridging alkylene group containing 1–3 carbon atoms, linking the α-carbon of the amino acid with the benzyl group. If the bridging alkylene group is a methylene A group, it is a homoamino acid. Examples of homologs of amino acids contemplated by the present invention include homoserine, homotyrosine, homocysteine, homophenylalanine, and the like. If the amino acid contemplated is a homoamino acid, it is designated as "hAA."

The amino acid residues, especially those containing aromatic as well as heterocyclic groups may be unsubstituted or be substituted with lower alkyl, lower arylalkyl, aryl, lower alkoxy, or hydroxy or electron withdrawing groups, as defined herein.

In the abbreviations described herein, the notation AA(YR) or its equivalent where Y is 0 or S, refers to an amino acid having an OR or SR group on the side chain, which side chain, as defined by the present invention, may be a hydroxy group, ether, thiol, or thioether. In these notations, the AA residue of AA(YR) refers to the amino acid where its side chain is less the hydroxy group, or thiol group, the thioether or ether group. Thus, AAYR refers to the amino acid wherein the YR group replaced the hydroxy, thio, thioether or ether group originally present. For example, in Ser(OBz), Ser refers to a serine moiety, less the hydroxy group on the side chain of the natural serine moieties and wherein the hydroxy group is replaced by benzyloxy. It is preferred each R is independently H, loweralkyl, aryl, lowerarylalkyl, heterocyclic or lowerheterocyclic alkyl.

The group Ser(OR) or Tyr(OR) or its request refers to a serine or tyrosine group in which the side chain contains a hydroxy or ether group. The group Cys(SR)or its equivalent refers to cysteine in which the side chain contains a thiol or a thioether. In addition, the group Phe($R_8$) or Tyr($R_9$) refers to a $R_8$ group or $R_9$ group, respectively, as defined herein, substituted on the phenyl ring of phenylalanine or tyrosine, respectively.

As defined herein, "a hydrophobic amino acid" is an amino acid containing a lower alkyl or aryl consisting of carbon and hydrogen atoms or aryl lower alkyl as the side chain. It is preferably a naturally occurring amino acid or homologs thereon, especially those homologs having 1–3 additional carbon atoms in the main side chain. The naturally occurring hydrophobic amino acids include such amino acids as Valine, Leucine, Isoleucine, Alanine, Tryptophan and Phenylalanine. Examples of hydrophobic homologs of amino acids include homophenylalanine and the like.

The term "hydroxy containing amino acids" or "thiol containing amino acid" refers to those naturally occurring amino acids having a hydroxy group or thiol group, respectively, on the side chain. The hydroxy group is connected to the α-carbon on the main chain of the amino acid by a bridging group which is preferably lower alkylene and lower arylalkylene, such as, for example, benzyl. Examples include serine, threonine, cysteine, tyrosine, homoserine, homocysteine, homotyrosine and the like.

The term "aromatic containing amino acid" refers to the naturally occurring amino acids having an aromatic group on the side chain. By aromatic, it is meant an aryl moiety containing only carbon ring atoms. It is preferred that the aromatic group contains 6–10 ring carbon atoms. It excludes heteroaromatics. The aromatic groups may be unsubstituted or substituted with electron withdrawing groups, as defined hereinbelow, or such electron donating groups as hydroxy, lower alkoxy, aryloxy, lowerarylalkoxy, or alkyl, aryl, or aryl lower alkyl. Preferably, the aromatic ring may be unsubstituted or substituted with various groups, such as alkyl, aryl, aryl lower alkyl, halo, hydroxy, lower alkoxy, aryloxy, lower aryl alkoxy, and the like. The alkyl groups, when used singly or in combination with respect to the substituents on the aromatic ring are preferably lower alkyl groups, as defined hereinbelow. Moreover, the term "aryl", as used herein is as defined hereinbelow. Examples of aromatic containing amino acids include Tyrosine, Tryptophan, and Phenylalanine.

As defined herein, when the amino acid residue has a hydroxy containing or thiol containing side group, the thiol or hydroxy group may be maintained or the hydrogen atom of the hydroxy or thio group is replaced with an aryl group, aryl lower alkyl group, an alkyl group, as defined hereinabove or a bulky alkyl group, thereby forming an ether or thioether, respectively.

As defined herein, the term "lower alkyl group" when used singly or in combination, refers to an alkyl group containing 1–6 carbon atoms. Examples include methyl, ethyl, propyl, isopropyl, butyl, sec-butyl, t-butyl, isopropyl, pentyl, neopentyl, hexyl, and the like.

The term "aryl" refers to an aromatic moiety containing 6–14 ring carbon atoms and up to a total of 20 carbon atoms. Examples include, phenyl, tolyl, xylyl, naphthyl, and the like.

"Aryl lower alkyl" signifies an alkyl group which is bridged to the main chain by a lower alkylene group as defined herein. Examples include benzyl, phenethyl and the like.

As used herein, the term "bulky alkyl group" refers to a tertiary alkyl group. Preferably it contains 4–10 carbon atoms, and more preferably 4–6 carbon atoms. Examples include tertiary butyl, neopentyl, 2,2-dimethylbutyl, and the like.

The term "electron withdrawing group" refers to a group which is more electronegative than hydrogen. Examples include nitro, cyano, halo, amido, carboxy, carboloweralkoxy, sulfonyl, sulfinyl, and the like, with the most preferred being a nitro or halo group.

The term heterocyclic, when used singly or in combination refers to a cyclic ring which may be saturated partly unsaturated or an heteroaryl and contain one, two or three hetero ring atoms. The heterocyclic rings include the benzoheterocyclics. The heterocyclic ring contain from 5–14 ring atoms. If it is preferred that the heterocyclic group contains 1, 2 or 3 ring heteroatoms selected from N, S or 0 and contain at least 2 carbon ring atoms and up to a total of 13 ring carbon atoms and up to a total of 18 carbon atoms. It is preferred that the hetercyclic ring is monocyclic or bicyclic and contains 5–10 ring atoms. Typical examples include thienyl, furyl, tetrahydrofuryl, oxazolyl, benzoxazolyl, pyrrolyl, pyridyl, imidazoyl, benzothienyl, pyranyl, pyrazolyl, pyrazinyl, indolyl, pyrimidinyl, isoquinolyl, quinolyl, piperidyl, morpholinyl, indolinyl, and the like.

As used herein, Z is an amino protecting group on the N-terminus end. Although it is not necessary that a protecting group on the N-terminus end be present (i.e., Z may be H), it is preferred that Z is a protecting group. These protecting groups block the amino group on the N terminal end of the amino acid or peptide.

A number of blocking reagents for amino groups are known in the art. Examples of amino protecting groups are described in an article entitled "Solid Phase Peptide Synthesis", by G. Barany and R. B. Merrifield in THE PEPTIDES, Vol. 2, edited by E. Gross and J. Meienhoffer, Academic Press, N.Y., N.Y. 100–118 (1980) and in the book entitled "PROTECTING GROUPS IN ORGANIC SYNTHESIS" by T. W. Green, John Wiley & Sons, New York, the contents of both of which are being incorporated by reference.

Examples of blocking groups include 9-lower alkyl-9-fluorenyloxycarbonyl, 2-chloro-1-indanylmethoxy-carbonyl (CLIMOC), benz[f]indene-3-methyloxycarbonyl (BIMOC), 2-(t-butyl sulfonyl)-2-propenyloxycarbonyl (Bspoc), benzothiophene sulfone-2-methoxycarbonyl (Bsmoc), t-butyloxycarbonyl (BOC), t-amyloxycarbonyl (Aoc), β-trimethylsilylethyloxycarbonyl (TEOC), adamantyloxycarbonyl (Adoc), 1-methylcyclobutyloxycarbonyl (Mcb), 2-(p-biphenylyl)propyl-2-oxycarbonyl (Bpoc), 2-(p-phenylazophenyl)propyl-2-oxycarbonyl (Azoc), 2,2-dimethyl-3,5-dimethyloxybenzyloxycarbonyl (Ddz), 2-phenylpropyl-2-oxycarbonyl (Poc), benzyloxycarbonyl (Cbz), Phthaloyl, piperidine-oxycarbonyl, formyl, acetyl, nicotinyl, i.e.,

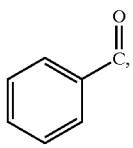

1,4-dihydrotrigomellyl, i.e.,

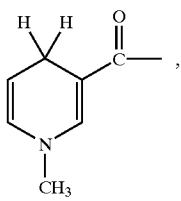

1-methylpyridinium$^{-3}$-acyl salt, e.g., the chloride salt,

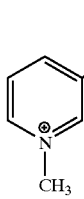 and the like.

It is preferred that a lipophilic amino protecting group is used, i.e., the protecting group contains a lipophilic moiety. For example, it is preferable that a moiety of the formula

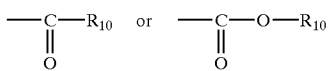

wherein $R_{10}$ is a lipophilic group, i.e., it is substantially non-polar. For example, $R_{10}$ is hydrocarbyl (containing only C and H atoms), silyl hydrocarbyl, (containing Si, C and H), or heterocyclic (containing C and H and ring N, O, or S atoms, containing up to 14 ring atoms, and 1, 2 or 3 ring heteroatoms, and 3–13 ring carbon atoms), including heteroaromatic. The blocking group, if present, is preferably sufficiently lipophilic to permit the compounds utilized in the present invention to diffuse or penetrate the cell membrane. It is especially preferred that Z is Cbz.

The inhibitors used in the present invention are preferably compounds of Formula I described hereinabove. The compounds of Formula I can also be depicted as below in Formula Ia:

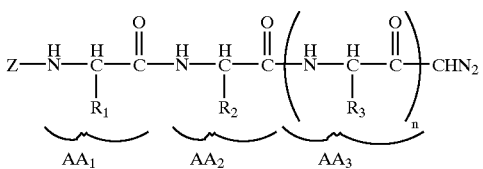

wherein Z and n are as defined hereinabove and $R_1$ $R_2$ and $R_3$ are independently side groups of amino acids, wherein $R_1$ refers to the side group of the amino acid of $AA_1$ as defined hereinabove, $R_2$ is the side group of the amino acid $AA_2$ as defined hereinabove and $R_3$ is the side group of the amino acid $AA_3$ as defined hereinabove.

It is preferred that $AA_1$ is a naturally occurring amino acid residue. Preferred values of $AA_1$ are Phe, hPhe, Val or Leu and most preferably Phe. When present, the preferred $AA_3$ is Serine, Threonine, Cysteine, homocysteine or homoserine, homotyrosine and especially tyrosine.

The preferred $AA_2$ is a hydrophobic naturally occurring amino acid. When n is 1, the preferred $AA_2$ is Leu; but when n is 0, it is preferred that $AA_2$ is Cit, Ala, Phe, hPhe, Thr (OR$_5$), Phe(R$_8$) hPhe(R$_8$), Aib, Met, Trp, Tyr(OR$_6$), Ser (OR$_4$), hSer(OR$_6$) or Val, wherein $R_5$ and $R_6$ are independently H, aryl (e.g. phenyl), lower aryl alkyl (e.g., benzyl) and especially bulkyl alkyl (e.g., t-butyl), $R_4$ is H, aryl (e.g. phenyl) and especially aryl alkyl (e.g., benzyl), and $R_8$ is H or an electron withdrawing substituent listed hereinabove, especially nitro or halo (e.g., I). With respect to $R_8$, it is preferred that the electron withdrawing group be in the ortho (2-position), and especially para (4-position) positions of the phenyl ring of the phenylalanine. It is more preferred that $AA_2$ is solely a hydroxy containing or thiol containing amino acid, and most preferably a hydroxy containing amino acid, especially tyrosine and serine which is unsubstituted or substituted as defined hereinabove.

In a preferred embodiment, n is 0.

It is more preferred that the compounds utilized in the invention have the formula:

$$Z-Phe-AA_2-CHN_2$$

wherein $AA_2$ is as defined hereinabove and more preferably is Ser(OR$_4$), Thr (OR$_5$), or Tyr(OR$_6$), hSer(OR$_4$) or hTyr (OR$_6$), wherein $R_4$, $R_5$ and $R_6$ are independently hydrogen, aryl, lower aryl alkyl or bulky alkyl and Z is a lipophilic amino protecting group.

The preferred $R_4$ value is aryl or lower aryl alkyl, especially benzyl.

It is preferred that $R_5$ and $R_6$ are bulky alkyl, e.g., neopentyl and especially t-butyl.

Preferred embodiments of the present invention include benzyloxycarbonyl-Phe-Ser(OBz)-CHN$_2$ (also known as CP-1), benzyloxycarbonyl-Phe-Tyr(OtBu)-CHN$_2$ (also known as CP-2), benzyloxycarbonyl-Phe-Cys-(SBz)-CHN$_2$, benzyloxycarbonyl-Phe-Cit-CHN$_2$, benzyloxycarbonyl-Phe-Ala-CHN$_2$, benzyloxycarbonyl-Phe (I) -Ala-CHN$_2$, benzyloxycarbonyl-Phe-Phe-CHN$_2$, benzyloxycarbonyl-Phe-Thr(O-t-Bu)-CHN$_2$, benzyloxycarbonyl-Phe-Phe (p-NO$_2$) -CHN$_2$, benzyloxycarbonyl-Phe-Aib-CHN$_2$, benzyloxycarbonyl-Leu-Met-CHN$_2$. benzyloxycarbonyl-Leu-Trp-CHN$_2$, benzyloxycarbonyl-Leu-Tyr-CHN$_2$, benzyloxycarbonyl -Leu-Leu-Tyr-CHN$_2$, and benzyloxycarbonyl-Val-Val-CHN$_2$, wherein Bz is benzyl, Aib is aminoisobutyric acid and Cit is citruilline.

The most preferred embodiments are CP-1 and CP-2.

Since the compounds utilized in the present invention are comprised of amino acids, and since each of the amino acids contain at least one chiral carbon atom, each amino acid moiety can exist in the D or L form. Thus, the compounds utilized in the present invention can exist in various stereoisomeric forms, including enantiomers, diastereoisomers, a combination thereof, as well as racemic mixtures. The use of all of these stereoisomers is contemplated to be within the scope of the present invention.

The compounds used in the present invention are either commercially available or are prepared by art recognized methods. An exemplary procedure is as follows:

For example, the compounds of the present invention are prepared by reacting the mixed anhydride of the corresponding peptide with diazomethane in an inert solvent, under conditions sufficient to form the diazomethyl ketone. The solvent utilized is inert to the peptide, the mixed anhydride thereof, reagents utilized to prepare the mixed anhydride and the product. Examples of the solvent that can be utilized include ether, especially lower alkyl ethers, such as diethyl ether, tetrahydrofuran, and the like. In an embodiment, the diazomethane in the inert solvent is added to the mixed anhydride. Inasmuch as diazomethane is quite reactive, the reaction is conducted at low temperatures, however, the temperature is sufficiently high to effect formation of the product but at a temperature lower than about 10° C. It is preferred that the reaction be conducted at a temperature at or below 50C.; and more preferably at a temperature at or above about −500° C. and at or below 5° C. It is more preferred that the reaction be initially conducted at about −25° C. up to a temperature of about 0C. In addition, it is preferred that the diazomethane be added dropwise to the mixed anhydride.

The mixed anhydride is prepared by reacting the peptide with an anhydride forming reagent, such as an acid halide, (e.g., an acid chloride) of a carboxylic acid containing 1–6 carbon acids, or lower alkyl ester thereof. An example of an anhydride forming reagent is isobutyl chloroformate.

The peptide is prepared by methodology-known in the art such as by, for example, reacting under amide forming conditions a first amino acid having a protecting group on the C-terminus and a second amino acid or acid halide thereof or ester thereof e.g., N-hydroxy succinimide ester, having a protecting group thereon, such as a benzyloxycarbonyl protecting group (Z-amino acid). A dehydrating agent, such as dicyclohexyl carbodiimide, may also be present. The protecting group on the C-terminus is then removed by methods known in the art. Examples of C-terminus protecting groups are known in the art and is described in the text, Protective Groups in Organic Synthesis, by Theodora W. Greene, John Wiley & Sons, 1981 ("Protective Groups") the contents of which are incorporated by reference. If a peptide larger than a dipeptide is desired, then the dipeptide described hereinabove is reacted under amide forming conditions with a third amino acid or acid derivative thereof, (e.g., halide, ester, and the like) in which the C-terminus is either unprotected or protected with a blocking group known in the art, e.g., a blocking group described in "Protective Groups". The process is repeated until the desired peptide is obtained. Alternatively in compounds comprised of tripeptides or higher, the smaller peptide units are prepared in a manner similar to that described hereinabove, and then the smaller peptide unit is reacted with an amino acid or acid derivative or another peptide or acid derivative under amide forming conditions, in accordance with the procedure described hereinabove, to form the desired higher peptide. Alternatively, the peptide is prepared by a combination of the procedures described herein.

As an illustration of the procedure, Z-AA$_1$—Osu, wherein Osu is the N-hydroxysuccinimide ester and Z is an amino protecting group, such as benzyloxycarbonyl, is reacted with H$_2$N—AA$_2$—OH in an equimolar ratio in DMF, triethylamine and dimethoxyethane under amide forming conditions. The product thereof is converted to the mixed anhydride and reacted with etheral diazomethane and after workup, the corresponding benzyloxycarbonyl peptidyl diazomethyl ketone compound is isolated.

The compounds described herein are administered to a patient in need thereof in therapeutically effective amounts.

As used herein, the term "patient" refers to a warm blooded animal such as a mammal which has tissue damage caused by ischemia. It is understood that guinea pigs, dogs, cats, rats, mice, horses, cattle, sheep, and humans are examples of animals within the scope of the meaning of the terms "mammal" and "patients"; it is preferred that the patient is human.

The term "therapeutically effective amount" refers to an amount which is effective, upon continuous infusion or upon single or multiple dose administration to the patient, in providing a reduction in the extent of damage resulting from ischemia, leading to an improved outcome and/or a delay or prevention of disease progression as compared to outcomes expected or obtained in the absence of treatment. The term "therapeutically effective amount" does not necessarily indicate a total elimination or cure of the tissue damage. In determining the therapeutically effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regiment selected; the use of concomitant medication; and other relevant circumstances. Based upon these factors, it is within the purview of the ordinary skilled artisan to determine the therapeutically effective amount to be administered to the patient.

A therapeutically effective amount of the compound described herein preferably ranges from about 0.01 milligram per kilogram of body weight per day (mg/kg/day) to about 100 mg/kg/day. Preferred amounts are expected to vary from about 0.5 to about 30 mg/kg/day.

In effecting treatment of a patient afflicted with a disease state described above, a compound utilized in accordance with the present invention can be administered in any form or mode which makes the compound bioavailable in effective amounts, including oral and parenteral routes. For example, it can be administered orally, subcutaneously, intramuscularly, intravenously, transdermally, intranasally, rectally, topically, and the like. Oral or intravenous administration is generally preferred. One skilled in the art of preparing formulations can readily select the proper form and mode of administration depending upon the particular characteristics of the compound selected for the disease state to be treated, the stage of the disease, and other relevant circumstances. The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds described herein, while effective themselves, may be formulated and administered in the form of their pharmaceutically acceptable salts, such as for example, acid addition salts, for purposes of stability, convenience of crystallization, increased solubility and the like.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds described herein may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound, i.e., the active ingredient, but this amount may be varied, depending upon the particular form and may conveniently be between about 4% to about 70% of the weight of the unit. The amount of the compound present in the pharmaceutical compositions is such that a suitable dosage will be obtained. It is preferred that an oral dosage unit form contains between about 5.0 and about 300 milligrams of the peptidyl diazomethyl ketones described herein.

The tablets, pills, capsules, troches and the like may also contain adjuvants typically utilized in the preparation of pharmaceuticals. They may include one or more of the following adjuvants: binders such as microcrystalline cellulose, gum tragacanth or gelatin; excipients such as starch or lactose, disintegrating agents such as alginic acid, corn starch and the like; lubricants such as magnesium stearate or zinc stearate; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil.

Other dosage unit forms may contain other materials which modify the physical form of the dosage unit, for example, as coatings. Thus, tablets or pills may be coated with sugar, shellac, or other enteric coating agents. A syrup may contain, in addition to the peptidyl diazomethyl ketone compounds described herein, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds may be incorporated into a solution or suspension. These preparations should contain at least 0.1% of the peptidyl diazomethyl ketone compound described herein, but the amount may be varied to be between 0.1 and about 50% of the weight thereof. The amount of the compound present in such compositions is such that a suitable dosage will be obtained. Preferred compositions and preparations are prepared so that a parenteral dosage unit contains between about 5.0 to about 100 milligrams of the active compound.

The compounds may also be administered topically, and when done so the carrier may suitably comprise a solution, ointment or gel base. Again, they are comprised of components normally utilized in preparing these types of pharmaceuticals. The base, for example, may comprise one or more of the following: petrolatum, lanolin, polyethylene glycols, bees wax, mineral oil, diluents such as water and alcohol, and emulsifiers and stabilizers. Topical formulations may contain a concentration of the compound or its pharmaceutical salts from about 0.1 to about 10% w/v (weight per unit volume).

The solutions or suspensions comprise ingredients normally utilized in these types of pharmaceuticals. For example, they may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As used herein, the singular shall include the plural and vice versa.

The preferred "hydrocarbyl" groups contain 1–20 carbon atoms.

Unless indicated to the contrary, the term "peptidyl diazomethyl ketone" refers to the free as well as the N-amino protected peptidyl diazomethyl ketone.

Unless indicated otherwise, percentages are by weight.

The following non-limiting examples further illustrate the present invention.

EXAMPLE 1

Benzyloxycarbonyl-Phe-Ser(OBz)-$CHN_2$ O-Benzyl-L-serine ($H_2$N-Ser(OBz)-OH)(1.95 g, 10 mmol) in dimethylformamide (10 ml), triethylamine (3 ml), and dimethoxyethane (10 ml) were stirred with N-α-benzyloxycarbonyl-L-phenylalanine N-hydroxysuccinimide ester (CBZ-Phe-Osu) (4.4 g, 10% excess) at room temperature. After stirring overnight, the reaction was diluted with water (150 ml) and extracted with ethyl acetate. The aqueous layer was acidified and the material which separated out was allowed to solidify. The crystallization was completed by cooling the mixture in an ice-water bath. The product was collected on a filter, washed with a small volume of cold water and dried over $P_2O_5$ in vacuo. The crude dipeptide acid (3.9 g) was recrystallized from hot ethyl acetate to yield 3.4 g.

The material was next converted to the diazomethyl ketone without further treatment.

The blocked dipeptide, CBZ-Phe-Ser (OBz)-OH (2.4 g, 5 mmol) was dissolved in tetrahydrofuran (20 ml) and chilled to −20° C., then N-methylmorpholine (458 μl, 4 mmol) followed by isobutyl chloroformate (542 μl, 4 mmol) were added. After 10 min, diazomethane (20 mmol) in diethyl ether was added, and the reaction mixture was first stirred for 1 h at −20° C., and then for 3 h at room temperature. Water (50 ml) was added, and the reaction mixture was extracted with ethyl acetate; the organic phase was washed successively with 10% $NaHCO_3$ and brine, and then dried over anhydrous $MgSO_4$, filtered and evaporated under reduced pressure. The product was chromatographed on silica gel with chloroform/methanol (49:1, v/v) and recrystallized from boiling ethyl acetate (mp 125–126° C.); the yield was 80%. The purity of the compound was checked by TLC and HPLC.

EXAMPLE 2

Benzyloxycarbonyl-Phe-Tyr-(OtBu)-$CHN_2$ A solution of 4-O-tert-butyl-L-tyrosine ($H_2$N-Tyr(O-t-Bu) -OH)(2.37 g, 10 mmol) in dimethylformamide (10 ml), triethylamine (3 ml), and 1,2-dimethoxyethane (10 ml) was stirred with N-α-benzyloxycarbonyl-L-phenylalanine N-hydroxysuccinimide ester (CBZ-Phe-Osu) (4.4 g, 11 mmol) at room temperature overnight. The reaction was diluted with water (100 ml) and extracted with ethyl acetate. The blocked dipeptide, N-α-benzyloxycarbonyl-L-phenylalanyl-O-tert-butyl-L-tyrosine (CBZ-Phe-Tyr(O-tBu)-OH), was liberated from the aqueous layer by acidification with 10% citric acid. The mixture was cooled in an ice-water bath for about 30 min, and the crystals which separated were collected and washed with a small volume of cold water. On further cooling, a second crop formed. The two crops were combined and dried under high vacuum in the presence of $P_2O_5$; the yield was 68%.

A portion of CBZ-Phe-Tyr(O-tBu)-OH (2.1 g, 4 mmol) obtained as described above was dissolved in tetrahydrofuran (20 ml), chilled to −20° C. and converted to the mixed anhydride with 3.2 mmol of N-methylmorpholine and isobutyl chloroformate. After 15 min, 40 ml of ethereal diazomethane at 0° C. was added, and the reaction mixture was left to warm gradually to room temperature and stirred for 3 hours. The reaction mixture was partitioned between cold aqueous NaHCO$_3$ and ethyl acetate. The organic layer was washed with aqueous NaCl, dried with anhydrous MgSO$_4$, filtered and evaporated under reduced pressure. The resulting solid (1.9 g) which indicated the presence of a major component on TLC, was chromatographed on Si60 (40 g) prepared in CH$_2$Cl$_2$. The sample was applied in 10% CH$_2$Cl$_2$ in methanol (10 ml) (v/v) and eluted with CH$_2$Cl$_2$ containing increasing amounts of methanol. The eluate was monitored by TLC. After examination by HPLC, the fractions were pooled and the solvents evaporated in vacuo. Recrystallization from ethyl acetate afforded the analytically pure dipeptidyl diazomethane product melting at 137–138° C.

EXAMPLE 3

CBZ-Leu-Leu-Pro-CHN$_2$ CBZ-Leu-Leu-OH was coupled with H-Pro-OMe, according to the methodology of Example 1. After hydrolysis with NaOH, the resulting acid was converted to the diazomethyl ketone in accordance with the procedure of Example 1.

EXAMPLE 4

Using the procedures described hereinabove in Example 1–3, and utilizing the appropriate peptide, the following compounds were also prepared:

CBZ-Phe-Cys(S-Bnzl)-CHN$_2$
CBZ-Phe-Ala-CHN$_2$
CBZ-Phe-Cit-CHN$_2$
CBZ-Phe(I)-Ala-CHN$_2$
CBZ-Phe-Phe-CHN$_2$
CBZ-Phe-Thr(O-t-Bu)-CHN$_2$
CBZ-Phe-Phe(p-NO$_2$)-CHN$_2$
CBZ-Phe-Aib-CHN$_2$
CBZ-Leu-Met-CHN$_2$
CBZ-Leu-Trp-CHN$_2$
CBZ-Leu-Tyr-CHN$_2$
CBZ-Leu-Leu-Tyr-CHN$_2$
CBZ-Val-Val-CHN$_2$.

The inventors have found that the peptidyl diazomethyl ketones described in the present application are specific inhibitors of cathepsin B or cathepsin L or both. In addition, they found that these are more effective in inhibiting these cysteine proteases than a compound which is a more general protease inhibitor. Moreover, the compounds used in the present invention are so specific that they do not substantially inhibit or block calpain and they are more effective inhibitors of cathepsin B or cathepsin L than calpain. The inhibitory effects and measurements thereof are described hereinbelow.

It is to be noted that it is difficult to ascribe a K$_1$ (inhibitor constant) value to a particular species of the proteinase in the reaction mixture, because active calpain undergoes autodigestion during kinetic studies. In situations like these, a comparison of the abilities of a compound to act as an inhibitor is measured by k$_{2app}$, a second order rate constant of inactivation.

Without wishing to be bound, it is believed that the mechanism of action of the peptidyl diazomethyl ketones described herein proceeds through a reversible complex followed by the formation of an irreversible covalent bond with the target enzyme. The process is represented by Eq. 1.

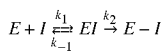  1 where E−I, EI, k$_1$ and k$_{-1}$ represent the reversible enzyme-inhibitor complex, the inactivated enzyme and the rate constants of the non-covalent reaction steps, respectively. With respect to k$_1$, it represents the rate constant for the formation of the reversible enzyme-inhibitor complex, while k$_{-1}$ represents the rate constant for the dissociation of the reversible-enzyme inhibitor complex, respectively, such that $$K_i = \frac{k_{-1}}{k_1}.$$

k$_2$ is the rate constant of the formation of the covalently modified enzyme.

Two methods are generally used to measure k$_2$, the rate constant for the formation of the inactivated enzyme.

The first method is described in Kitz, R. and Wilson, L. B., *J. Biol. Chem.*, 1962, 237, 3243–3249, the contents of which are incorporated by reference. In this method, the proteinase (calpain, cathepsin B or cathepsin L) and a large excess of inhibitor are mixed together, such that the concentration of the inhibitor, such as the peptidyl diazomethyl ketone is significantly greater than the enzyme concentration. At various times, after mixing, various samples are taken and the residual enzyme activity a$_t$ is determined using standard techniques known to the artisan of ordinary skill, such as by diluting the sample into a solution of fluorogenic substrate. Under these conditions, the EI complex is dissociated and the fraction of the initial enzyme activity, a$_t$, remaining at time t is calculated as follows:

$$\ln a_t = k_2 t/(1+K_i/[I]) \qquad 2$$

A plot of ln a$_t$ against time gives the observed rate of inactivation k$_{obs}$.

$$k_{obs} = k_2/(1+K_i/[I]) \qquad 3$$

Rearranging the equation, equation 3 becomes $$[I]/k_{obs} = \frac{K_i}{k_2} + \frac{[I]}{k_2} \qquad 4$$

$$\frac{k_2}{k_{obs}} = \frac{K_i}{I} + 1 \qquad 5$$

$$\frac{k_2}{K_i} = \frac{k_{obs}}{[I]} + \frac{[I]}{K_i} \qquad 6$$

Since the measurements are made under conditions where [E]<<[I]<<K$_i$, the saturation effect of EQ 6 becomes $$\frac{k_2}{K_i} = \frac{k_{obs}}{[I]} = k_{2app} \qquad 7$$

The value of $$\frac{k_2}{K_i}$$

is $k_{2app}$.

The kinetic analysis may also be done by adding the enzyme to a mixture of the substrate and the inhibitor, and monitoring the formation of the product of the enzymatic reaction, and its progress curve until it reaches a limiting product concentration $[P]_\infty$, when all of the enzyme has been inactivated. The product concentration $[P]_t$ at a time t after mixing is given by $$[P]_t=[P]_\infty(1-e^{-k_{obs}[I]t}) \qquad 8$$

wherein
EQ 8 becomes $$\ln([P]_\infty-[P]_t)=\ln[P]_\infty-k_{obs}[I]t \qquad 9$$

$k_{obs}$ and hence $k_2$ are obtained from the slopes of the plot of EQ 9, in accordance with the procedure of Tian, et al., *Biochemistry* 1982, 1028–1032. ("Tian, et al.") the contents of which are incorporated by reference. More specifically, the value of $k_{obs}$ is given by the slope of a plot of ln $[P]_\infty-[p]_t$ versus t (time). The apparent second-order rate contact for inactivation, $k_{2app}$ was calculated as $k_{obs}/[I]$. The inactivation-rates ($k_{obs}$) in the presence of substrate and for different inhibitor concentrations for calpain, cathepsin B and cathepsin L are determined according to the method of Tian, et al. However, $k_{2app}$ is corrected for the presence of substrate (s) to give the second order rate constant $k^1_{2app}$, calculated as $k^1_{2app}=k_{2app}(1+[s]/Km)$. In the experiments, the following Km values are used for the correction factor for $k^1_{2app}$: 0.4 μM for calpain, 0.39 μM for cathepsin B and 2.4 μM for cathepsin L.

The latter methodology was used to measure the inactivation rate constant of various inhibitors as described hereinbelow.

EXAMPLE 5

Calpain was assayed fluorimetrically in 1 ml of 50 mM Tris/acetate buffer, pH 7.5, containing 5 mM $CaCl_2$, 2.5 mM DTT(dithiothreitol), 0.1% Triton X-100 at 37° C., using $2.5 \times 10^{-4}$ M Suc-Leu-Tyr-aminomethylcoumarin (AMC) (Novabiochem, Switzerland) as substrate and 50nM (final concentration) of enzyme. The appearance of the 7-amino-4 methylcoumarin product was recorded continuously with a Perkin Elmer 650-10S spectrofluorimeter, a SPEX Fluorolog 1680, or SLM 8000C fluorescence spectrometer with excitation at 370 nm and emission at 460 nm.

Inhibitors and substrate were added to the assay buffer but without calcium in a thermostated fluorimeter cuvette as DMSO solutions where the DMSO content of the final mixture did not exceed 4%. Typically, 5 μL of the substrate solution (50 mM stock in DMSO) was added to 1 mL of buffer. Varying concentrations of the inhibitor solution (10 μL of a DMSO Rio solution) were added, followed by 10 μL of calpain in the assay buffer. After allowing the reaction mixture to incubate for 2–5 min, during which time a steady baseline level of fluorescence was measured, calcium was added in a 10-μL volume to initiate hydrolysis of the fluorogenic substrate, and the resulting increase in fluorescence was monitored continuously. When inhibitors were tested at very low concentrations, the enzyme concentration was reduced to maintain a minimum of a 10-fold excess of inhibitor over enzyme.

Cathepsins B and L were preactivated with 1 nM DTT in 50 mM sodium acetate buffer, pH 5.4, 1 mM EDTA for 2 h at 4° C. and assayed in the same buffer with 0.01% Brij [poly(oxyethylene) glycol dodecyl ether]. 5 μM (final concentration) CBZ-Phe-Arg-AMC was used as substrate for both for cathepsins B and L. The inhibitors (0.1–1 μM) and substrate were added to the reaction mixture to incubate for 5 min in a cuvette thermostated at 30° C. Then, approximately 0.4 nM and 0.1 nM final concentration of cathepsin B and cathepsin L, respectively, were used to initiate the reaction. Progress curves for the inactivation of the proteinases were monitored fluorimetrically ($\lambda_{ex}$=370 nm, $\lambda_{em}$=460 nm) The rate of fluorescence increase of the aminomethylcoumarin product was observed to decrease exponentially to give a rate essentially equal to zero (<2% of initial rate of fluorescence increase). The progress curves were analyzed over at least 3 half lives to calculate the rate constants of inactivation in accordance with the procedure described by Crawford, C. Mason, R. W., Wilkström, P., and Shaw, E. in an article entitled "The design of peptidyldiazomethane inhibitors to distinguish between the cysteine proteinases calpain II, cathepsin L and cathepsin B.", *Biochem. J.* 1988, 253, 751–758, the contents of which are incorporated by reference. The rates of inactivation of various substrates are tabulated hereinbelow. The $K_m$ values used were 2.4 μM and 150 M for cathepsin B and cathepsin L, respectively.

The data is tabulated hereinbelow.

| Inhibitor | Calpain $k'_{2app}$ ($M^{-1}S^{-1}$) | Cathepsin B $k'_{2app}$ ($M^{-1}S^{-1}$) | Cathepsin L $k'_{2app}$ ($M^{-1}S^{-1}$) |
|---|---|---|---|
| CBZ-Phe-Ser(OBz)-$CHN_2$ | <10 | 8,800 | 1,000,000 |
| CBZ-Phe-Tyr(OtBu)-$CHN_2$ | <10 | 10 | 200,000 |
| CBZ-Phe-Cys(SBnz1)-$CHN_2$ | N.D. | 30,000 | 390,000 |
| CBZ-Phe-Ala-$CHN_2$ | <5 | 1,200 | 160,000 |
| CBZ-Phe-Cit-$CHN_2$ | N.D. | 6,700 | 1,800,000 |
| CBZ-Phe(I)-Ala-$CHN_2$ | N.D. | 980 | 130,000 |
| CBZ-Phe-Phe-$CHN_2$ | N.D. | 350 | 140,000 |
| CBZ-Phe-Thr(OtBu)-$CHN_2$ | N.D. | 160 | 60,000 |
| CBZ-Phe-Phe(pNO$_2$)-$CHN_2$ | N.D. | 50 | 190,000 |
| CBZ-Phe-Aib-$CHN_2$ | Not yet screened | Not yet screened | Not yet screened |
| CBZ-Leu-Met-$CHN_2$ | N.D. | 4,060 | 212,000 |
| CBZ-Leu-Trp-$CHN_2$ | N.D. | <50 | 12,000 |
| CBZ-Leu-Tyr-$CHN_2$ | 1,470 | <50 | 1,500,000 |
| CBZ-Leu-Leu-Tyr-$CHN_2$ | 230,000 | 1,300 | 1,500,000 |
| Substrate | Suc-Leu-Tyr-AMC | Z-Arg-Arg-AMC | Z-Phe-Arg-AMC |

It is preferred that the compounds of the present invention exhibit an inactivation rate constant value for either cathepsin B or cathepsin L greater than or equal to 10 $M^{-1}S^{-1}$. It is also preferred that the inactivation rate constant value for the compounds of the present invention with respect to either one of cathepsin B or cathepsin L is greater than 6 times that of the inactivation rate constant value with respect to calpain. It is even more preferred that the inactivation rate constant value for the compounds of the present invention with respect to either cathepsin B or cathepsin L is greater than about ten times that of the inactivation rate constant value for calpain.

As indicated hereinabove, the compounds of the present invention are specific inhibitors of one of cathepsin B or L or both.

By being specific inhibitors of cathepsin B or cathepsin L, the compounds of the present invention do not exhibit unwanted side effects with other cysteine proteases.

For example, the compounds utilized in the present invention do not substantially inhibit caspases. Caspase is another type of cysteine protease, which is believed to play a role in neuronal apotosis after ischemia. These enzymes comprise the interleukin B converting enzyme (ICE) family of cysteine proteases. It is believed that caspases participate in the process of delayed cell death by breaking down cell structures such as the nuclear membrane which directly precede chromatin condensation, a hallmark of apoptosis.

Another advantage of the present invention is that the peptidyl diazomethyl ketones utilized in the present invention, do not substantially inhibit caspases. Without wishing to be bound, it is believed that inhibitors of caspases require aspartic acid or glutamic acid at the P-1 position, which position in Formula I ($AA_1$) is occupied by an hydrophobic amino acid residue, which, by definition, cannot be aspartic or glutamic acid.

The compounds of the present invention are inhibitors of very specific enzymes, viz., cathepsin B or cathepsin L or both. Without wishing to be bound, it is believed that this specificity is accomplished by the presence of the diazomethyl ketone group. In addition, if a lipophilic amino protecting group is also present, such as benzyloxy carbonyl, it is believed, without wishing to be bound, that it also attributes to the specificity of the compounds utilized in the present, invention.

The lipophilic amino protecting group, such as benzyloxycarbonyl group, is located on the N-terminus amino end of the peptide. Since it is lipophilic, its ability to interact with other enzymes is reduced. Moreover, the diazomethylketone function on the C-terminus does not react with other proteases because of the chemical stability. Without wishing to be bound, it is believed that the diazomethylketones are stable as a result of the resonance structure of the diazocarbonyl structure; this reduces the ability of these agents to non-selectively alkylate other biomolecules.

Obviously, the peptidyl diazomethyl ketones described in the present application would not be effective unless cathepsin B or cathepsin L play a key role in causing tissue damage from ischemia. The present inventors have found that cathepsin B and/or cathepsin L activity increases after cerebral ischemia and do cause tissue damage.

The inventors have used a stroke model in rats, explained in more detail hereinbelow, to verify this. In this model, a nylon monofilament is advanced through the vasculature of anesthetized rats until it blocks the middle cerebral artery. The monofilament is left in place for two hours. Withdrawal of the monofilament initiates reperfusion of the ischemic tissue. The extent of damage is visualized seven days after the ischemic event by removing the brain of the animal and examining it in section.

Immunohistological analysis of tissue sections of the brains of animals treated in this way at several time points after reperfusion was initiated established that cathepsin B was released in the ischemic tissue for at least two hours after reperfusion. However, at 24 hours after reperfusion was initiated, there was no difference in the distribution of the activity between the two brain hemispheres. Similarly, samples of the tissue from these areas at the earlier time points demonstrated increased cathepsin B activity in the ischemic brain and increased synthesis of cathepsin B mRNA. Control experiments established that the increased cathepsin B activity occurred only upon reperfusion of the ischemic tissue.

The initial cathepsin inhibitor used by the inventors was a large naturally occurring molecule, stefin A (MW 15,000). In the stroke model, this molecule was administered intraventricularly in some studies prior to the occlusion and intravenously upon reperfusion in others. In both cases administration of the inhibitor was associated with about a 40% reduction in the volume of the infarcted brain tissue compared to animals that did not receive the inhibitor.

Stefin A is a control, which is an inhibitor of cathepsin; however, it is not a good clinical candidate due to its large molecular weight, its elaborate recombinant preparation technique and its propensity to inhibit proteases nonselectively. To overcome these detrimental characteristics of this inhibitor, the inventors chose the small lipophilic molecules described hereinabove.

The effectiveness of the peptidyl diazomethane ketones are illustrated in the following examples performed in vivo.

PROTOCOL FOR EXAMPLES 6–9

In the following experiments, the following stroke model was utilized.

Male Wistar rat weighing between 270–290 gm are fasted the night prior to surgery. Each rat was then anesthetized with 3.5% halothane, and spontaneously respired with 0.5% halothane in a 2:1 $N_2O:O_2$ mixture using a face mask. A normal range of blood gases and pH is maintained during ischemia and reperfusion with the face mask inhalation, as verified by samples taken from a femoral artery PE-50 catheter. Body temperature is maintained constant at 37° C. with a recirculating heating pad and K module with an intrarectal type T thermocouple. The PE-50 catheters are inserted into the femoral artery and vein following induction of anesthesia to obtain the blood gas, glucose and hemoglobin concentrations and to monitor blood pressure.

The right common carotid artery, external carotid artery and internal carotid artery are isolated using microsurgical techniques. A clamp is applied to the common carotid artery and a 4-0 nylon suture with a rounded tip is inserted into the external carotid artery through a small puncture. The clamp on the common carotid artery is removed. The suture is passed distally into the internal carotid artery until it blocks the middle cerebral artery. Two hours after the MCA occlusion, the animal is again anesthetized, and the nylon suture is removed from the internal carotid artery.

Infusion of the inhibitor or vehicle is done by intravenous infusion via the femoral vein.

The animal is able to move about and take water as needed. However, animals with severe stroke that are not able to maintain intake of water are supplemented with daily subcutaneous Lactated Ringers solution. Daily body weights are followed to assess nutritional status.

INTRAVENOUS INFUSION STUDIES

Syringe pumps were filled under sterile conditions with either isotonic saline/1% DMSO solution as the control or with the concentration of CP-1 or CP-2 indicated in the examples, hereinbelow. The pumps delivered the solution at a rate of 15 $\mu$l/min for up to 4 hours.

After anesthesia had been induced in the rat, a catheter was inserted into the femoral vein and tunneled subcutaneously in the posterior neck region. Body temperature was maintained at a constant temperature of 37° C. during surgical procedures. The animals underwent 2 hours of MCA occlusion, and then reperfusion when the suture was withdrawn, and immediately thereafter, the drug was infused for four hours. The animals were killed after a 7-day reperfusion, and the brains were formalin fixed and sliced 6-μm thick into seven coronal sections A–G, and mounted on coated slides. After staining with hematoxylin and eosin, the stroke volume was measured using an image analysis program. The stroke area and the contralateral hemispheric area were calculated by tracing the areas on the computer screen, and the volumes were determined by multiplying the appropriate area by the section interval thickness. The stroke volume is expressed as the percentage of lesion size to the volume of contralateral hemisphere. Statistical analysis was performed using the independent t-test.

EXAMPLE 6

CP-1 dissolved in 1% DMSO and isotonic saline was given intravenously to Wistar rats (15 μl/min) at concentrations of 2 μM, 10μM, 50μM and 25μM for 4 hours immediately after reperfusion following two hours of MCA occlusion, in accordance with the procedure described hereinabove. Control animals underwent a similar protocol but they had injected therein 1% DMSO/Saline as the vehicle within four hours. All animals which survived 7 days were sacrificed and the stroke volume calculated. The results are tabulated hereinbelow:

| Group | % Hemisphere Infarct Volume (% ± SEM) |
|---|---|
| Control (N = 10) | 37 ± 2.6 |
| CP-1 (10 μM) (N = 10) | 22 ± 4.7, p = 0.01 |
| CP-1 (50 μM) (N = 10) | 20 ± 4.1, p = 0.003 |
| CP-1 (250 μM) (N = 8) | 23 ± 5.2, p = 0.02 |
| CP-1 (2 μM) (N = 7) | 39 ± 2.1, p > 0.1 |

EXAMPLE 7

The protocol described hereinabove was repeated with CP-2 used in lieu of CP-1, at doses of 10, 50, 250 and 500 μM.

The results are tabulated hereinbelow:

| Group | % Hemisphere Infarct Volume (% ± SEM) |
|---|---|
| Control (N = 10) | 37 ± 2.6 |
| CP-2 (10 μM) (N = 10) | 28 ± 4.6, p > 0.05 |
| CP-2 (50 μM) (N = 10) | 35 ± 4.8, p > 0.05 |
| CP-2 (250 μM) (N = 10) | 21 ± 4.7, p = 0.01 |
| CP-2 (500 μM) (N = 9) | 22 ± 3.5, p = 0.004 |

The data from these examples show that all doses of CP-1 except 2 μM reduced the area of damage from 37% of the cerebral hemisphere to about 20%. High doses of CP-2 were effective, but not the lower doses. Therefore, these data show treated animals had about half the stroke damage of control animals.

Moreover, since these compounds reached the brain while retaining their activity, another conclusion is drawn. The compound used in the present invention can cross the blood-brain barrier and do not react indiscriminately with biomolecules.

These data clearly show that both cathepsin B and L contribute to neuronal destruction after transient focal cerebral ischemia has occurred. Such ischemic cell damage is significantly reduced by the specific inhibitors of cathepsin B or cathepsin L utilized in the present method.

EXAMPLE 8

CP-1 dissolved in 1% DMSO and isotonic saline was given intravenously to Wistar rats (15 μl/min) at a concentration of 50 μM for four hours beginning at the end of three hours of MCA occlusion, in accordance with the protocol described hereinabove. Control animals underwent a similar protocol, but they had injected therein a 1% DMSO/Saline as the vehicle for four hours beginning at the end of a three hour MCA occlusion. All animals which survived 7 days were sacrificed and the infarct volume was measured 7 days after the MCA occlusion. The results are tabulated hereinbelow.

| Treatment | % Hemisphere Infact Volume (% ± SEM) |
|---|---|
| Control | 41.1 ± 2.4 |
| CP-1 | 39.9 ± 4.1 |

The values are the mean iSEM of the results from 8 or 9 animals. P>0.05 according to the Mann-Whitney Rank test.

On the first day and on the seventh day after occlusion, the neurological function was determined on a four point scale (0, 1, 2, 3,) as described in an article by Bederson, et al. in *Stroke*, 1986, 17:472–476, the contents of which are incorporated by reference.

The neurological status was determined as follows:

Rats were held gently by the tail and were suspended one meter above the floor and were observed for 5 flexion of the forelimb.

A grade of 0 was given to the rats who extended both forelimbs to the floor and exhibited no other neurological deficit (i.e., normal rat). If the rat exhibits any amount of consistent forelimb flexion and no other abnormality, they were assigned a grade of 1. (These rats had a mild infarction).

The rats were placed on large sheet of soft, plastic coated paper (such as counter protection paper) which they could potentially firmly grip with their claws. The tail of the rats were held by hand, and gentle lateral pressure was applied behind the rat's shoulder until it was noticed that the forelimbs slid several inches. This maneuver was repeated several times in each direction. If the rats exhibited decreased resistance to the lateral push toward the paretic side and decreased resistance to forelimb flexion, without circling, they were graded 2. (These rats were severely dysfunctional).

Rats which exhibited the same behavior as those graded 2 but additionally exhibited circling toward the paretic side when allowed to move freely were graded 3.

Using this assessment, the following results were obtained:

| Group | Functional Score Day 1 | Functional Score Day 7 |
|---|---|---|
| Control | 3 ± 0 | 1.9 ± 0.3 |
| CP-1 | 2.1 ± 0.6 | 0.9 ± 0.2 |

These values are the mean score ±SEM of the results from treatment on control animals. P≦0.05 according to the Mann Whitney Rank Sum test.

The % loss of body weight from CP-1 treated animals and the control group on Day 1 and Day 7 are tabulated hereinbelow.

| Group | Day 1 | Day 7 |
|---|---|---|
| Control | 19 ± 2.0 | 32 ± 3.0 |
| CP-1 | 16 ± 1.4 | 28 ± 3.4 |

As the data indicates, no significant difference in the loss of mean body weight between treated and control animals was observed on Day 1 and Day 7 after the two hour MCA occlusion. Moreover, the results further show that CP-1 at the mid range of the effective doses in the 2 hour MCA occlusion was not effective in reducing infarct size in the 3 hour MCA occlusion; however, it was effective in reducing the neurological deficits due to the occlusion.

The following experiment was performed to show that CP-1 reduces cathepsin B activity in the brain in vivo.

EXAMPLE 9

CP-1 dissolved in 1% DMSO was prepared as in Example 6.

The protocol of Example 6 was followed except as follows: the rats under went two hours of MCA occlusion, they were administered either CP-1 (50 $\mu$M) or 1% DMSO/saline for four hours after reperfusion and the rats were sacrificed after 48 hours of survival.

At that time, the brains were extracted and separated with right and left, cortical and subcortical regions and immediately frozen in liquid nitrogen. The samples were homogenized with buffer, titrated, and then reacted with the substrate CBZ-Arg-Arg-AMC with the resultant fluorescence measured with a fluorophotometer. Activity is expressed in units of enzyme activity per mg of soluble brain protein (mean +SEM). The results are tabulated hereinbelow:

CATHEPSIN B ACTIVITY IN CONTROL CP-1 TREATED ANIMAL

| Group | Control | CP-1 |
|---|---|---|
| Left Cortex (N = 6) | 0.142 ± 0.02 | 0.106 ± .01 |
| Right Cortex (N = 6) | 0.181 ± 0.04 | 0.113 ± 0.01 |
| Right Subcortex (N = 6) | 0.198 ± 0.03 | 0.113 ± 0.02* |
| Left Subcortex (N = 6) | 0.147 ± 0.02 | 0.084 ± .01* |

* $p < 0.05$ (independent t-test)

Each value was obtained, in both the control and CP-1 treated groups from six animals.

As clearly shown by the data, the animals that received infusion of CP-1 had significantly lower cathepsin B activity in the subcortical regions, compared to animals that received vehicle solution only. This data further demonstrate that CP-1 infusion reduces effective brain activity of cathepsin B when given after two hours of MCA occlusion.

The peptidyl diazomethyl ketone of the present invention, as indicated hereinabove, are useful for the treatment of tissue damage caused by ischemia. For example, once administered, the peptidyl diazomethyl ketones of the present invention substantially retarded or arrested further tissue damage caused by the ischemia, such as stroke or myocardial infarction. For example, from animal studies, it has been shown that the administration of peptidyl diazomethyl ketones described herein to animals with strokes reduced the severity of the neurological damage resulting from the stroke, so that those animals to whom these compounds were administered exhibited improved neurological function scores relative to the non-treated animals. Other data has shown that the administration of the peptidyl diazomethyl ketone described herein to animals suffering from a cerebral infarction, results in a reduction in the size of the infarction and of the infarct volume relative to the non-treated animals.

Without wishing to be bound, it is believed that the peptidyl diazomethyl ketones are effective because they inhibit cathespin B or cathepsin L. These enzymes are believed to be involved in one of the steps in the cascade of reactions that results in tissue damage. By inhibiting one or both of these enzymes, it is believed that the compounds of the present invention prevent the enzymes from functioning in this cascade of reactions, thereby retarding and/or arresting any further tissue damage from occurring.

As indicated hereinabove, the compounds of the present invention are administered to patients who have suffered from an ischemia. The most beneficial effects of compounds of the present invention are realized if the compounds of the present invention are administered to the patient as quickly as possible after be occurrence of the ischemia. It is, however, preferred that the compounds of the present invention are first administered within six hours of the ischemia, more preferably within three hours after the ischemia and most preferably within two hours of the ischemia. Although the peptide diazomethyl ketone can be administered to the patient for several days after the occurrence of the ischemia, e.g., stroke or myocardial infarction, the most beneficial effects are seen within the first few hours of administration. Accordingly, it is preferred that the peptidyl diazomethyl ketones described in the present invention are administered up to about 36 hours after the occurrence of the ischemia, more preferably up to about 24 hours after the occurrence of the ischemia, and most preferably up to about ten hours after the occurrence of the ischemia.

The administration of the peptidyl diazomethyl ketone to a patient, as described hereinabove, prevents further tissue damage from occurring. As a result, theses drugs have a prophylactic effect, which characteristic can be exploited during surgical operations in ways which were not feasible heretofore. For example, if during surgery, it is necessary to clamp off or occlude an artery in the brain or heart, such as in cerebral aneurysm surgery or open heart surgery, the present invention provides a way to effect such clamping without significantly causing tissue damage. This is effected by administrating the peptidyl diazomethyl ketones described in the instant specification prior to and during the surgical procedure and preferably after the completion of the surgical procedure. If the patient is unconscious, the peptidyl diazomethyl ketones can be administered by routes known to the skilled artisan, ordinary, such as intravenously. Such a protocol will minimize any tissue damage that may result from the clamping of the artery. After the surgical procedure is completed, it is preferred that the peptidyl diazomethyl ketones be administered for additional time, e.g., up to thirty-six hours, as described hereinabove.

The above preferred embodiments and examples are given to illustrate the scope and spirit of the present invention. The embodiments and examples described herein will make apparent to those skilled in the art other embodiments and examples. These other embodiments and examples are within the contemplation of the present invention. Therefore, the present invention should be limited only by the appended claims.

What is claimed is:

1. A method of treating tissue damage in a patient caused by ischemia comprising administering to said patient a therapeutically effective amount of a compound which is a specific inhibitor of either cathepsin B or cathepsin L, but which is not as effective an inhibitor of calpain relative to either cathepsin B or cathepsin L, said compound having a molecular weight of about 450 to about 1000 daltons and being a peptidyl diazomethyl ketone which is either unprotected or has an N-terminus amino protecting group.

2. The method according to claim 1 wherein said compound is a dipeptide or tripeptide.

3. The method according to claim 1 wherein the compound is a specific inhibitor of cathepsin B.

4. The method according to claim 1 wherein the compound is a specific inhibitor of cathepsin L.

5. The method according to claim 1 wherein the ischemia is myocardial ischemia.

6. The method according to claim 1 wherein the ischemia is cerebral ischemia.

7. The method according to claim 1 wherein the compound additionally does not substantially inhibit caspase.

8. The method according to claim 1 wherein the compound is not an inhibitor of calpain.

9. The method according to claim 1 wherein said compound has an N-terminus amino protecting group.

10. The method according to claim 9 wherein the N-terminus amino protecting group is CBZ, wherein CBZ is benzyloxycarbonyl.

11. The method according to claim 1 wherein the compound has the formula:

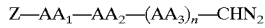

Z—AA$_1$—AA$_2$—(AA$_3$)$_n$—CHN$_2$ wherein

Z is an N-terminus amino protecting group or hydrogen;

n is 0 or 1;

AA$_1$ is a hydrophobic amino acid;

AA$_3$, when present, is a naturally occurring hydroxy or thiol containing amino acid;

AA$_2$ is a hydrophobic amino acid when n is 1 or when n is 0;

AA$_2$ is Met, Cit, Aib, Trp, Ala, Ser (OR$_4$), Thr (OR$_5$), Tyr(R$_9$) (OR$_6$), hTyr(R$_9$) (OR$_{10}$), Cys(SR$_7$), hCys(SR$_7$) hSer (OR$_4$), hPhe(R$_8$) or Phe(R$_8$);

hTyr is homotyrosine;

hCys is homocysteiene;

hSer is homoserine;

hPhe is homophenylalanine;

R$_4$, R$_5$, R$_6$ and R$_7$ are independently hydrogen, lower alkyl, aryl, aryl lower alkyl, lower alkyl or bulky alkyl group;

R$_8$ is hydrogen an electron withdrawing group; and

R$_9$ is hydrogen or electron withdrawing group.

12. The method according to claim 11 wherein the compound additionally does not substantially inhibit caspase.

13. The method according to claim 1 wherein the compound has the formula:

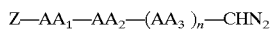

Z—AA$_1$—AA$_2$—(AA$_3$)$_n$—CHN$_2$ wherein

Z is an N-terminus amino protecting group or hydrogen;

n is 0 or 1;

AA$_1$ is a hydrophobic amino acid;

AA$_3$ is a hydrophobic amino acid, AA$_4$ (OR$_{12}$) or AA$_5$ (SR$_{12}$); and AA$_2$ is α-amino butyric acid or a hydrophobic amino acid residue when n is 1, but when n is 0, AA$_2$ is a hydrophobic amino acid residue, AA$_4$(OR$_{11}$) or AA$_5$ (SR), hAA$_4$(OR$_{11}$), hAA$_5$(SR$_{11}$) or Met;

AA$_4$ and AA$_5$ are independently amino acids in which the OH, SH or S—CH$_3$ groups on the side chain are deleted;

hAA$_4$ is a homo amino acid of AA$_4$;

hAA$_5$ is a homo amino acid of AA$_5$; and

R$_{11}$ and R$_{12}$ are independently hydrogen, lower alkyl, aryl, aryllower alkyl, heterocyclic or hetercyclic lower alkyl.

14. The method according to claim 13, wherein n is 1, and AA$_3$ is a hydrophobic acid, Ser(OR$_{12}$), hSer(OR$_{12}$), Cys (OR$_{12}$), hCys (OR$_{12}$), Thr(OR$_{12}$), Tyr(OR$_{12}$) or hTyr(OR$_{12}$).

15. The method according to claim 13 wherein n is 0 and AA$_2$ is a hydrophobic amino acid residue, Met, Ser(OR$_{11}$), hSer(OR$_{11}$), Cys(OR$_{11}$), hCys(OR$_{11}$), Thr(OR$_{11}$), Tyr (OR$_{11}$), hTyr(OR$_{11}$).

16. The method according to claim 13 wherein AA$_1$ is a naturally occurring amino acid.

17. The method according to claim 13 wherein AA$_2$ is a naturally occurring amino acid where n is 1.

18. The method according to claim 13 wherein AA$_1$ is Phe.

19. The method according to claim 13 wherein n is O.

20. The method according to claim 13 wherein

AA$_1$, is Phe, Leu, or Val;

AA$_2$ is Cys(S-Benzyl), hCys(S-Benzyl), hSer(O-Benzyl), hPhe(PNO$_2$), Ser(O-Benzyl) Thr(O-Benzyl), Tyr(Ot-Bu), Tyr(I), Tyr(I)(Ot-Bu), Ala, Cit, Phe, Thr(Ot-Bu), Phe-(pNO$_2$), Aib, Met, Trp, Tyr or Val when n is 0, or AA$_2$ is Leu when n is 1; and AA$_3$ is Tyr.

21. The method according to claim 13 wherein

AA$_1$ is Phe, Leu or Val; and

AA$_2$ is Cys(S-Benzyl), Cit, Ala, Phe, Thr (O-t-Bu), Val, Phe(p-NO$_2$), Aib, Met, Trp, Tyr, Tyr(Ot-Bu), Tyr(I), Tyr(I) (Ot-Bu), Ser(O-Benzyl), or Thr-(O-Benzyl).

22. The method according to claim 13 wherein the compound additionally does not substantially inhibit caspase.

23. The method according to claim 13 wherein the compound is CBZ-Phe-Ser(O-Benzyl)-CHN$_2$, CBZ-Phe-Tyr-(O-t-Bu)-CHN$_2$, CBZ-Phe-Cys(S-Benzyl)-CHN$_2$, CBZ-Phe-Cit-CHN$_2$, CBZ-Phe-Ala-CHN$_2$, CBZ-Phe(I)-Ala-CHN$_2$, CBZ-Phe-Phe-CHN$_2$, CBZ-Phe-Thr(O-t-Bu)-CHN$_2$, CBZ-Phe-Phe(p-NO$_2$)-CHN$_2$, CBZ-Phe-Aib-CHN$_2$, CBZ-Leu-Met-CHN$_2$, CBZ-Leu-Trp-CHN$_2$, CBZ-Leu-Tyr-CHN$_2$, CBZ-Leu-Leu-Tyr-CHN$_2$ or CBZ-Val-Val-CHN$_2$, wherein CBZ is benzyloxy.

24. The method according to claim 23, wherein the compound is Z-Phe-Ser-(O-Benzyl)-CHN$_2$ or Z-Phe-Tyr (Ot-Bu)-CHN$_2$.

25. The method according to claim 13 wherein the N-amino protecting group is

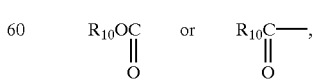

$$R_{10}O\underset{\underset{O}{\|}}{C} \quad \text{or} \quad R_{10}\underset{\underset{O}{\|}}{C}\text{—},$$

wherein R$_{10}$ is a lipophilic group.

26. The method according to claim 25 wherein the N-amino protecting group is CBZ, wherein CBZ is benzyloxycarbonyl.

27. The method according to claim 26 wherein $R_6$ is bulky alkyl.

28. The method according to claim 27 wherein $R_6$ is t-butyl.

29. The method according to claim 13 wherein the compound has the formula:

$$Z—AA_1—AA_2—CHN_2$$

wherein Z is an N-amino protecting group at the N-terminus end;

$AA_1$ is Phe, Ala, Leu, Ile, or Val, hPhe;

$AA_2$ is Met, Cit, Aib, Trp, Ala, Val, Ser($OR_4$), hSer($OR_4$), Thr($OR_5$), Tyr($R_9$) ($OR_6$), Cys($SR_7$), hCys($SR_7$), Phe($R_8$) hTyr($R_9$) ($OR_6$), hPhe($R_8$);

hTyr is homotyrosine;

hPhe is homophenylalanine;

hSer in homoserine;

hCys is homocysteine;

$R_4$, $R_5$, $R_6$ and $R_7$ are independently hydrogen, aryl, aryl lower alkyl or bulky alkyl group; and $R_8$ and $R_9$ are independently an electron withdrawing group or hydrogen.

30. The method according to claim 29 wherein $AA_1$ is Phe.

31. The method according to claim 29 wherein the compound has the formula:

$$Z—Phe—AA_2—CHN_2$$

wherein $AA_2$ is Ser($OR_4$), hSer($OR_4$), Thr($OR_5$), or hTyr ($OR_6$), Tyr($OR_6$) and $R_4$, $R_5$ and $R_6$ are bulky alkyl, aryl or aryl lower alkyl.

32. The method according to claim 29 wherein $AA_2$ is Ser($OR_4$), Thr($OR_5$), Tyr($OR_6$) or Cys($SR_7$).

33. The method according to claim 32 wherein $R_4$, $R_5$ and $R_7$ are independently aryl or aryl lower alkyl.

34. The method according to claim 33 wherein $R_4$, $R_5$ and $R_7$ are benzyl.

35. A method for preferentially inhibiting a protease selected from the group consisting of cathepsin B and cathepsin L relative to the protease calpain in a patient comprising administering to said patient a therapeutically effective amount of a compound selected from the group consisting of peptidyl diazomethyl ketone and a N-terminus amino protected peptidyl diazomethyl ketone, wherein said compound is a specific inhibitor of said cathepsin B or cathepsin L and is a more effective inhibitor of either of cathepsin B or cathepsin L relative to calpain, the inactivation rate constant value of said compound relative to cathespin B or cathepsin L being greater than 6 times that of the inactivation rate constant of calpain and wherein the compound is a dipeptide or tripeptide.

36. The method according to claim 35 wherein the compound additionally does not substantially inhibit caspase.

37. The method according to claim 35 wherein the compound is $$Z—AA_1—AA_2—(AA_3)_n—CHN_2$$

wherein

Z is an N-terminus amino protecting group or hydrogen;

n is 0 or 1;

$AA_1$ is a hydrophobic amino acid;

$AA_3$ is a hydrophobic amino acid, $AA_4(OR_{12})$ or $AA_5(SR_{12})$; and $AA_2$ is α-amino butyric acid or a hydrophobic amino acid residue when n is 1, but when n is 0, $AA_2$ is a hydrophobic amino acid residue, $AA_4(OR_{11})$ or $AA_5(SR_{11})$, h$AA_4(OR_{11})$, h$AA_5(SR_{11})$ or Met;

$AA_4$ and $AA_5$ are independently amino acids in which the OH, SH or S—$CH_3$ groups on the side chain are deleted;

h$AA_4$ is a homo amino acid of $AA_4$;

h$AA_5$ is a homo amino acid of $AA_5$; and $R_{11}$ and $R_{12}$ are independently hydrogen, lower alkyl, aryl, aryllower alkyl, heterocyclic or hetercyclic lower alkyl.

38. The method according to claim 35 wherein the compound is not an inhibitor of calpain.

39. The method according to claim 38 wherein the compound has the formula $$Z—AA_1—AA_2—(AA_3)_n—CHN_2$$

wherein

Z is an N-terminus amino protecting group or hydrogen;

n is 0 or 1;

$AA_1$ is a hydrophobic amino acid;

$AA_3$ is a hydrophobic amino acid, $AA_4(OR_{12})$ or $AA_5(SR_{12})$; and $AA_2$ is α-amino butyric acid or a hydrophobic amino acid residue when n is 1, but when n is 0, $AA_2$ is a hydrophobic amino acid residue, $AA_4(OR_{11})$ or $AA_5(SR_{11})$, h$AA_4(OR_{11})$, h$AA_5(SR_{11})$ or Met;

$AA_4$ and $AA_5$ are independently amino acids in which the OH, SH or S—$CH_3$ groups on the side chain are deleted;

h$AA_4$ is a homo amino acid of $AA_4$;

h$AA_5$ is a homo amino acid of $AA_5$; and $R_{11}$ and $R_{12}$ are independently hydrogen, lower alkyl, aryl, aryllower alkyl, heterocyclic or hetercyclic lower alkyl.

40. The method according to claim 39 wherein Z is CBZ, wherein CBZ is benzyloxycarbonyl.

41. A method of reducing neurological damage resulting from a stroke comprising administering to a patient suffering from a stroke, a therapeutically effective amount of a compound which is a specific inhibitor of either cathepsin B or cathepsin L, but which is not as effective an inhibitor of calpain relative to either cathepsin B or cathepsin L, and said compound having a molecular weight of about 450 to about 1000 daltons and being a peptidyl diazomethyl ketone which is either unprotected or has an N-terminus amino protecting group.

* * * * *